United States Patent [19]

Ahmed et al.

[11] Patent Number: 4,757,148
[45] Date of Patent: Jul. 12, 1988

[54] INTERMEDIATE 1-(2-NITRO-1-IMIDAZOLYL)-3-SUBSTITUTED AMINO-2-PROPANOLS AND THE CORRESPONDING 2,3-BUTANEDIOLS

[75] Inventors: Israr Ahmed, London; Gerald E. Adams, Epsom Downs; Ian J. Stratford, Oxted; David Gibson, London, all of England

[73] Assignee: National Research Development Corporation, England

[21] Appl. No.: 929,095

[22] Filed: Nov. 10, 1986

Related U.S. Application Data

[62] Division of Ser. No. 498,827, May 27, 1983, Pat. No. 4,631,289.

[30] Foreign Application Priority Data

May 27, 1982 [GB] United Kingdom ............... 8215545
Nov. 1, 1982 [GB] United Kingdom ............... 8231107

[51] Int. Cl.$^4$ .......................................... C07D 233/95
[52] U.S. Cl. .................................................. 548/338
[58] Field of Search .......................................... 548/338

[56] References Cited

U.S. PATENT DOCUMENTS

4,241,060 12/1980 Smithen ............................. 548/336
4,282,232 8/1981 Agrawal ............................. 548/336

FOREIGN PATENT DOCUMENTS

0000928 3/1979 European Pat. Off. ............ 548/336
2003154 3/1979 United Kingdom ................. 548/336

OTHER PUBLICATIONS

Stratford, Int. J. Radiation Biol. Phys., vol. 8, 391–392 (1982).
Smith et al., Chemical Abstracts, vol. 95 (1981) No. 17999S.
Cancer-vol. 48, No. 3, Aug. 1, 1981—American Cancer Society Inc., J. P. Lippincott Company—696–707.
Hypoxia Mediated Radiation and Chemo—Sensitizing Drugs Br. J. Cancer (1984), 50, 285–289.
Radiation Sensitization and Chemopotentiation: RSU 1069, a Compound More Efficient than Misonidazole-Br. J. Cancer (1984) 49, 571–577.

*Primary Examiner*—Richard A. Schwartz
*Assistant Examiner*—Kurt G. Briscoe
*Attorney, Agent, or Firm*—Jacobs & Jacobs

[57] ABSTRACT

A compound of formula I

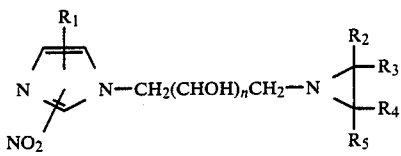

in which formula:
$R_1$ represents hydrogen or an alkyl group;
$R_2$–$R_5$ represent hydrogen, alkyl aryl, aralkyl or alkaryl group; and
n is 1 or 2.

4 Claims, No Drawings

INTERMEDIATE 1-(2-NITRO-1-IMIDAZOLYL)-3-SUBSTITUTED AMINO-2-PROPANOLS AND THE CORRESPONDING 2,3-BUTANEDIOLS

This is a division of Ser. No. 498,827 filed May 27, 1983, now U.S. Pat. No. 4,631,289.

This invention relates to compounds useful in the treatment of cancer patients by radiotherapy or chemotherapy, to a process for the production of such compounds, to formulations for administration and to methods of treating such patients.

Accordingly, the present invention comprises a compound of formula I

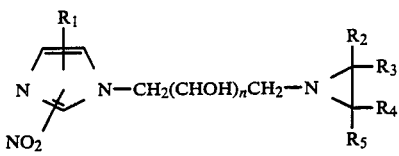

in which formula:
- $R_1$ represents hydrogen or an alkyl (e.g. $C_1$–$C_6$ alkyl) group;
- $R_2$–$R_5$ represent hydrogen, alkyl (e.g. $C_1$–$C_6$ alkyl), aryl, aralkyl or alkaryl group; and
- n is 1 or 2.

In compounds I, the nitro group is typically located at the 2-position on the imidazole ring and $R_1$, when an alkyl group, e.g. a methyl group, is usually disposed at the 5-position. Generally, at least two of $R_2$–$R_5$ are hydrogen and preferably at least one of $R_2$–$R_5$ is an alkyl, e.g. a methyl, ethyl or isopropyl group or a benzyl group. Compounds wherein the group —$NO_2$ is located at the 2-position, $R_1$ represents hydrogen, n is 1 and $R_2$, $R_3$, $R_4$ and $R_5$ represent hydrogen or $R_2$ and $R_3$ represent methyl and $R_4$ and $R_5$ represent hydrogen or $R_2$ and $R_4$ represent methyl and $R_3$ and $R_5$ represent hydrogen are of particular interest.

The compounds are useful in increasing the sensitivity of tumour cells to radiation in radiotherapy and also in potentiating or enhancing damage to tumours by chemotherapeutic agents.

A compound I may be produced, in accordance with a further aspect of the present invention from compound II by treatment thereof with an aziridine of formula III preferably in a polar solvent such as an alcohol.

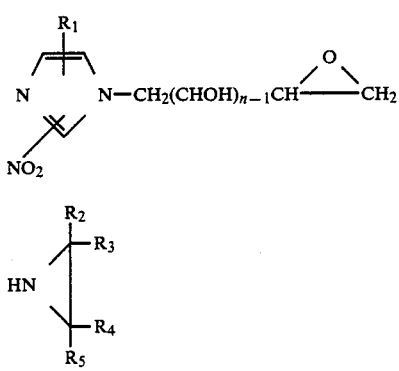

In a second process within the scope of the present invention for the production of the compound I, the compound of formula II is reacted with a compound of formula IIIA:

$$H_2NCR_2R_3CR_4R_5-X \qquad \text{IIIA}$$

wherein X represents a halogen, typically chlorine or bromine, preferably in the presence of an acid acceptor e.g. an alkali metal hydroxide.

In a third process within the scope of the present invention for the production of the compound I, a compound IV

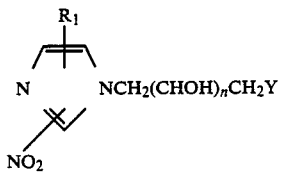

wherein Y represents a halogen, typically bromine or chlorine, is reacted with an aziridine of formula III, preferably in the presence of an acid acceptor e.g. an alkali metal hydroxide.

In a fourth process within the scope of the present invention for the production of the compound I, a compound V

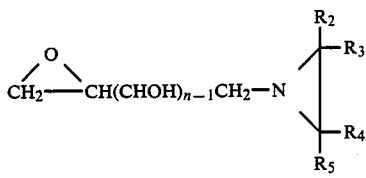

is reacted with a compound of formula VI

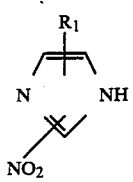

preferably under neutral or basic conditions.

In a fifth alternative process within the scope of the present invention for the production of the compound I, a compound of formula VII:

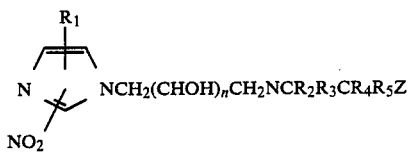

wherein Z represents a halogen, typically bromine or chlorine, is cyclised by treatment with a base, typically an alkali metal hydroxide e.g. potassium or sodium hydroxide.

The above alternative processes are typically conducted in a polar solvent such as an alcohol.

When n is 2, compound I may be prepared by reaction of a compound of formula VIII with an aziridine of formula III suitably in a polar solvent such as methanol:

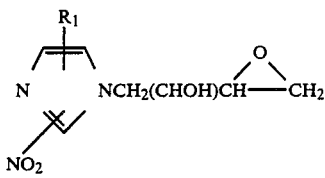

Intermediate compounds of formula VIII also form part of the present invention.

The compound I may be formulated in a manner appropriate to the treatment for which it is to be used by bringing it into association with a pharmaceutically compatible carrier or diluent. The compound may be included in a dosage form such as a tablet or capsule, for example a capsule comprising known formulation components such as one or more of those described in Example A of U.K. Patent Application No. 2003154A. The compound may also be formulated for intravenous administration e.g. in a saline drip solution.

When employed as a radiation sensitizing agent, in accordance with a further aspect of the present invention, the compound I is administered to a patient having a radiation sensitive cancer prior to irradiation of said cancer.

The compound I may, however, in yet a further aspect of the present invention be employed for chemopotentiation of a chemotherapeutic agent by administration of the compound I to a patient having a localised or metastatic cancer. Administration of the compound I is generally carried out prior to or simultaneously with administration of the chemotherapeutic agent, for example melphalan, cyclophosphamide, 5-fluorouracil or CCNU (1-(2-chloroethyl)-3-cyclohexyl-1-nitrosourea).

The invention is illustrated by the following Examples:

EXAMPLE 1

1-(2-Nitro-1-imidazolyl)-3-(1-aziridino)-2-propanol

A mixture of 1-(2,3-epoxypropyl)-2-nitroimidazole prepared by the method described by Beaman (Beaman A. G., Tautz W. and Duschinsky R., 1967; Studies in the Nitroimidazole Series, Antimicrobial Agents and Chemotherapy p. 520–530), (5.10 g, 0.03 mol) and aziridine (2.60 g., 0.06 mol) in methanol (70 ml) is heated under reflux for one hour. The reaction mixture is treated with decolourising charcoal, refluxed for 5 minutes and filtered. The solvent is removed under reduced pressure to a yellow residue, which is dissolved in a minimum quantity of ethanol and allowed to crystallise to give 1-(2-Nitro-1-imidazolyl)-3-(1-aziridino)-2-propanol (3.57 g, 56%, m.p. 119°–121° C.) as a pale yellow crystalline solid. Recrystallization causes the decomposition of the product.

EXAMPLE 2 AND 3

In the following Examples, WHT mice in which the MT tumour has been implanted subcutaneously are administered the compound of Example 1 intraperitoneally before treatment with radiation or with the chemotherapeutic agent melphalan. The time before such treatment at which the drug is administered is such that maximum enhancement is effected. The results of treatment with radiation and the chemotherapeutic drug are set out respectively in Tables I and II together with comparison results using misonidazole (MISO) and the compound Ro-03-8799. The asterisks against the results from treatment with the latter compounds indicate that the tumours treated in these cases are intramuscular.

TABLE I

|  | MISO | 8799 | Compound I |
|---|---|---|---|
| Example 2 Radiosensitization |  |  |  |
| Administered dose mmoles/kg | 3.8 | 3.8 | 3.8 |
| Enhancement ratio | 1.3 | 1.3 | 1.7 |
| Example 3 Chemosensitization (melphalan) |  |  |  |
| Administered dose mmoles/kg | 0.72 | 0.72 | — |
| Enhancement ratio | 1.7* | 2.2* | — |
| Administered dose mmoles/kg | — | 0.72 | 0.08 |
| Enhancement ratio | — | 1.9 | 3.0 |

EXAMPLE 4

1-(2-Nitro-1-imidazolyl)-3-(2-methyl-1-aziridino)-2-propanol

In a manner analogous to that described in Example 1 there is obtained by reaction of 2-methyl aziridine with 1-(2,3-epoxypropyl)-2-nitroimidazole after crystallization from ethanol-ether, 1-(2-nitro-1-imidazolyl)-3-(2-methyl-1-aziridino)-2-propanol in the form of a pale yellow crystalline solid (3.06 g, 45%, m.p. 109°–111° C.).

EXAMPLE 5

1-(2-Nitro-1-imidazolyl)-3-(2-ethyl-1-aziridino)-2-propanol

In a manner analogous to that described in Example 1 there is obtained by reaction of 2-ethylaziridine with 1-(2,3-epoxypropyl)-2-nitroimidazole after crystallization from ethanol-ether at −70° C., 1-(2-nitro-1-imidazolyl)-3-(2-ethyl-1-aziridino)-2-propanol in the form of a pale yellow crystalline solid which changes to a yellow thick oil at room temperature; yield 65%.

EXAMPLE 6

1-(2-Nitro-1-imidazolyl)-3-(2-benzyl-1-aziridino)-2-propanol

In a manner analogous to that described in Example 1, but using equimolar amounts of reagents, there is obtained from reaction of 2-benzyl aziridine with 1-(2,3-epoxypropyl)-2-nitroimidazole after column chromatography using silica gel as adsorbent, 1-(2-nitro-1-imidazolyl)-3-(2-benzyl-1-aziridino)-2-propanol in the form of a pale yellow gum, in 72% yield.

EXAMPLE 7

1-(2-Nitro-1-imidazolyl)-3-(2,2-dimethyl-1-aziridino)-2-propanol

In a manner analogous to that described in Example 1, there is obtained from reaction of 2,2-dimethyl aziridine with 1-(2,3-epoxypropyl)-2-nitroimidazole after crystallization from ethanolether, 1-(2-nitro-1-imidazolyl)-3-(2,2-dimethyl-1-aziridino)-2-propanol in the form of a pale yellow crystalline solid of melting point 101°–103° C.; yield 78%.

EXAMPLE 8

1-(2-Nitro-1-imidazolyl)-3-(2-phenyl-1-aziridino)-2-propanol

The compound is preparable by reaction of 1-(2,3-epoxypropyl)-2-nitroimidazole with 2-phenylaziridine (K. Ichimura and M. Ohta, Bull. Chem. Soc. Japan, 43(5) 1443–50 (1970)) in methanol, following the method described in Example 1.

EXAMPLE 9

1-(2-Nitro-1-imidazolyl)-3-(2-isopropyl-1-aziridino)-2-propanol

The compound is preparable by reaction of 1-(2,3-epoxypropyl-2-nitroimidazole with 2-isopropylaziridine (K. Ichimura, Bull. Chem. Soc. Japan 43 1443–50 (1970)) in methanol following the method described in Example 1.

EXAMPLE 10

1-(2-Nitro-1-imidazolyl)-4-(1-aziridino) or substituted aziridino)-2,3-butane-diol. (I, $R_1$=H, n=2, $R_2$–$R_5$=H or alkyl, aryl, aralkyl, or alkaryl)

(a) 1-(2-nitroimidazolyl)-2-hydroxy-3,4-epoxy butane 3-(2-Nitroimidazolyl)-2-hydroxy-1-butene (11.83 gms, m.p. 90°–92° C., prepared by refluxing a mixture of azomycin, 1,3-butadiene monoxide and anydrous potassium carbonate in ethanol for 5 hours) is stirred overnight in dichloroethane with m-chloroperbenzoic acid in the presence of 3-tert-butyl-4-hydroxy-5-methylphenyl sulfide and after stirring the reaction mixture is refluxed for 1 hour. The mixture is washed with saturated sodium carbonate solution and the aqueous phase was extracted with chloroform. The combined dichloroethane and chloroform extracts are concentrated to a small volume and the product is purified by column chromatography, in which silica gel is the stationary phase and a mixture of chloroform (90%) and ethanol (10%) the eluent. The product is crystallized from ethanol as a pale yellow solid of m.p. 134°–136° C. Yield 33%.

(b) The compound from (a) is reacted with an aziridine of formula III in methanol to yield the required compound of formula I.

EXAMPLE 11

1-(2-methyl-5-nitro-1-imidazolyl)-3-(1-aziridino or substituted aziridino)-2-propanol. (I, $R_1$=CH$_3$, n=1, $R_2$–$R_5$=H alkyl, aryl, aralkyl or alkaryl)

1-(2,3-epoxypropyl)-2-methyl-5-nitroimidazole (M. Hoffer and E. Grunberg, J. Med. Chem. 17, 1019 (1974)) is reacted with an aziridine of formula III in methanol to yield the required compound of formula I.

EXAMPLE 12

1-(2-methyl-4-nitro-1-imidazolyl)-3-(1-aziridino or substituted aziridino)-2-propanol. (I, $R_1$=CH$_3$, n=1, $R_2$–$R_5$=H alkyl, aryl, aralkyl or alkaryl)

The procedure of Example 11 is repeated using 1-(2,3-epoxypropyl)-2-methyl-4-nitroimidazole (J. Suwinski, E. Suwinska, J. Watras (1974) and M. Widel, Acta Pol. Pharm., 15(5), 529 (1975)) to yield the required compound of formula I.

EXAMPLES 13 AND 14

1-(2-Nitro-1-imidazolyl)-3-(2,3-dimethyl-1-aziridino)-2-propanol (meso and dl forms)

A mixture of meso and dl forms of 2,3-dimethylaziridine, prepared by the method of Dickey described in J. Amer. Chem Soc. Vol. 74, p 944 (1952), is reacted with 1-(2,3-epoxypropyl)-2-nitroimidazole in a manner analogous to that described in Example 1, to yield a mixture of the meso and dl forms of 1-(2-nitro-1-imidazolyl)-3-(2,3-dimethyl-1-aziridino)-2-propanol (isomers reflect the presence of two chiral centres in the aziridinyl moiety). The meso and dl forms are separated by column chromatography in which silica gel is the stationary phase and a mixture of diethyl ether (95%) and ethanol (5%) the eluant. The meso form has m.p. 84°–5° and the dl form is isolated as a waxy solid.

Sensitisation and toxicity data for compounds described in the above Examples are set out in Table II.

TABLE II

Sensitisation and toxicity data on Compounds described in the Examples

| Example number | $R^1$ | Position of NO$_2$ group | n | $R_2$ | $R_3$ | $R_4$ | $R_5$ | $C_{1.6}$/mol dm$^{-3a}$ | LD$_{50}$/mmol/kg$^b$ | Therapeutic ratio$^d$ relative to Compound of Example 1 |
|---|---|---|---|---|---|---|---|---|---|---|
| 1 | H | 2 | 1 | H | H | H | H | $1.0 \times 10^{-4}$ | 0.61$^c$ | 1 |
| 4 | H | 2 | 1 | Me | H | H | H | $8 \times 10^{-5}$ | <0.58 | <1.2 |
| 6 | H | 2 | 1 | PhCH$_2$ | H | H | H | | | |
| 5 | H | 2 | 1 | Et | H | H | H | $1.3 \times 10^{-4}$ | 0.58 | 0.73 |
| 7 | H | 2 | 1 | Me | Me | H | H | $8 \times 10^{-5}$ | 1.25 | 2.56 |
| 8 | H | 2 | 1 | Ph | H | H | H | $3 \times 10^{-4}$ | | |
| 13 | H | 2 | 1 | Me(meso) | H | Me | H | $8 \times 10^{-5}$ | ≧1.25 | 2.56 |
| 14 | H | 2 | 1 | Me(dl) | H | Me | H | $8 \times 10^{-5}$ | | |
| 10 | H | 2 | 2 | H | H | H | H | $1.3 \times 10^{-4}$ | 0.41 | 0.52 |
| 11 | 2-Me | 5 | 1 | H | H | H | H | $3 \times 10^{-4}$ | 0.80 | 0.44 |
| 12 | 2-Me | 4 | 1 | H | H | H | H | | | |

TABLE II-continued
Sensitisation and toxicity data on Compounds described in the Examples

| Example number | $R^1$ | Position of $NO_2$ group | n | $R_2$ | $R_3$ | $R_4$ | $R_5$ | $C_{1.6}$/mol dm$^{-3a}$ | $LD_{50}$/mmol/kg$^b$ | Therapeutic ratio$^d$ relative to Compound of Example 1 |
|---|---|---|---|---|---|---|---|---|---|---|
| 9 | H | 2 | 1 | Me$_2$CH— | H | H | H | $1.3 \times 10^{-4}$ | $\geq 1.18$ | 1.49 |

$^a$Concentration required to achieve an enhancement ratio of 1.6 in irradiated hypoxic V79 mammalian cells.
$^b$Drugs administered i.p. to ♀ WHT mice.
$^c$For Compound of Example 1 in ♂ CRCD1 mice $LD_{50} = 0.71$ mmole/kg ⎫ administered  $LD_{50}$ 0 0.87 mmole/kg ⎫ administered
$LD_{10} = 0.54$ mmole/kg ⎭ i.p.           $LD_{10} = 0.71$ mmole/kg ⎭ i.v.

$^d \dfrac{LD_{50}}{C_{1.6}} \times \dfrac{10^4}{0.61}$ — Higher value is more efficacious.

We claim:

1. A compound of formula (VII):

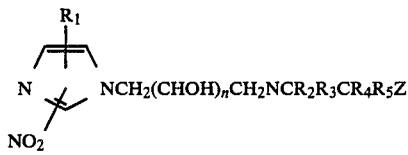
(VII)

wherein
$R_1$ is hydrogen or alkyl of from 1 to 6 carbon atoms,
$R_2$, $R_3$, $R_4$ and $R_5$ is hydrogen, alkyl of from 1 to 6 carbon atoms, carbocyclic aryl or carbocyclic arylalkyl having from 1 to 6 carbon atoms in the alkyl moiety,
Z is halogen, and
n is 1.

2. A compound according to claim 1, wherein said carbocyclic aryl is substituted by alkyl of from 1 to 6 carbon atoms.

3. A compound of formula (VII):

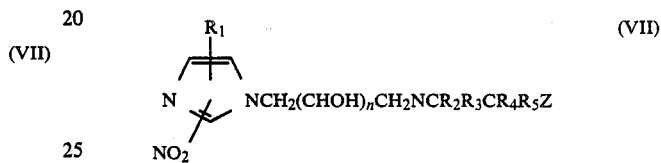
(VII)

wherein
$R_1$ is hydrogen or alkyl of from 1 to 6 carbon atoms,
$R_2$, $R_3$, $R_4$ and $R_5$ is hydrogen, alkyl of from 1 to 6 carbon atoms, carbocyclic aryl or carbocyclic arylalkyl having from 1 to 6 carbon atoms in the alkyl moiety,
Z is halogen, and
n is 2.

4. A compound according to claim 3, wherein said carbocyclic aryl is substituted by alkyl of from 1 to 6 carbon atoms.

* * * * *

UNITED STATES PATENT AND TRADEMARK OFFICE
CERTIFICATE OF CORRECTION

PATENT NO. : 4,757,148
DATED : July 12, 1988
INVENTOR(S) : ISRAR AHMED ET AL

It is certified that error appears in the above-identified patent and that said Letters Patent is hereby corrected as shown below:

At Column 2, in formula (VII) between Lines 50 and 59, delete "$NCH_2(CHOH)_nCH_2NCR_2R_3CR_4R_5Z$" and substitute therefor -- $NCH_2(CHOH)_nCH_2NHCR_2R_3CR_4R_5Z$ --.

At Column 7, Claim 1, in formula (VII) between Lines 20 and 28, delete "$NCH_2(CHOH)_nCH_2NCR_2R_3CR_4R_5Z$" and substitute therefor -- $NCH_2(CHOH)_nCH_2NHCR_2R_3CR_4R_5Z$ --.

At Column 8, Claim 3, in formula (VII) between Lines 19 and 27, delete "$NCH_2(CHOH)_nCH_2NCR_2R_3CR_4R_5Z$" and substitute therefor -- $NCH_2(CHOH)_nCH_2NHCR_2R_3CR_4R_5Z$ --.

Signed and Sealed this

Twenty-first Day of February, 1995

Attest:

Attesting Officer

BRUCE LEHMAN

Commissioner of Patents and Trademarks